United States Patent
Bealin-Kelly

(10) Patent No.: US 6,306,429 B1
(45) Date of Patent: Oct. 23, 2001

(54) CONFECTIONERY COMPOSITIONS

(75) Inventor: Francis Joseph David Bealin-Kelly, Surrey (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/403,376

(22) PCT Filed: Apr. 14, 1998

(86) PCT No.: PCT/IB98/00557

§ 371 Date: Oct. 20, 1999

§ 102(e) Date: Oct. 20, 1999

(87) PCT Pub. No.: WO98/47483

PCT Pub. Date: Oct. 29, 1998

(30) Foreign Application Priority Data

Apr. 21, 1997 (GB) ................................................ 9707979

(51) Int. Cl.[7] .............................. A61K 47/00; A61K 9/68; A61K 9/36; A61K 9/14; A01N 59/14
(52) U.S. Cl. ........................... 424/439; 424/440; 424/479; 424/489; 426/660
(58) Field of Search ..................................... 424/439, 440, 424/451, 479, 489; 426/660

(56) References Cited

U.S. PATENT DOCUMENTS

| | | |
|---|---|---|
| 3,894,154 | 7/1975 | Graff et al. .............................. 426/5 |
| 4,136,163 | 1/1979 | Watson et al. .......................... 424/54 |
| 4,157,402 | 6/1979 | Ogawa et al. ............................. 426/5 |
| 4,230,688 | 10/1980 | Rowsell et al. ......................... 424/45 |
| 4,250,196 | 2/1981 | Friello ................................... 426/658 |
| 4,372,942 | * 2/1983 | Cimiluca ................................ 424/16 |
| 4,466,983 | 8/1984 | Cifrese et al. ........................... 426/5 |
| 4,517,205 | * 5/1985 | Aldrich ................................. 426/103 |
| 4,762,719 | * 8/1988 | Forester ................................ 424/440 |
| 5,002,791 | 3/1991 | Knebl .................................... 426/660 |
| 5,458,894 | 10/1995 | Knebl et al. ........................... 426/231 |
| 5,698,181 | * 12/1997 | Luo ........................................ 424/49 |

FOREIGN PATENT DOCUMENTS

| | | |
|---|---|---|
| 0140085 | 9/1984 | (EP) . |
| 0431376 | 11/1990 | (EP) . |
| 0534823 | 9/1992 | (EP) . |
| 1452291 | 8/1973 | (GB) . |
| 9702273 | 1/1997 | (WO) . |
| 9706695 | 2/1997 | (WO) . |
| WO 97/06695 | * 2/1997 | (WO) . |

* cited by examiner

Primary Examiner—Thurman K. Page
Assistant Examiner—S. Tran
(74) Attorney, Agent, or Firm—Loy M. White; John M. Howell

(57) ABSTRACT

Throat drops suitable for relief of cough and cold symptoms comprise a cooling composition and a warming composition in distinct and discrete regions thereof, the cooling and warming compositions being adapted to provide sequential relief profiles. The cooling composition includes from about 0.001% to about 10%, by weight, cooling agent, and the warming composition comprises from about 0.001% to about 1.0%, by weight, warming agent.

28 Claims, No Drawings

1

CONFECTIONERY COMPOSITIONS

This application is a 371 of PCT/IB98/00557 filed Apr. 14, 1998.

FIELD OF THE INVENTION

The present invention relates to centre-filled confectionery compositions, especially liquid centre-filled confectionery compositions, providing an enhanced perception of throat warming or cooling.

BACKGROUND OF THE INVENTION

Products in the form of cough syrups and candy-based cough drops have long been known as vehicles for the delivery of medicaments aimed at soothing sore or irritated throats. Such medicaments include analgesics, antitussives, expectorants, cooling agents such as menthol, and warming agents such as ethanol or gingerol. The material can be administered swallowing a liquid cough mixture or by way of a throat drop or lozenge which releases the active agent upon sucking. Particularly in the case of a volatile active agent, the product can also provide relief from cold symptoms by way of clearing the nasal passages.

EP-A-431,376 describes hard confections for sustained release treatment of sore throats comprising hydrogenated isomaltulose and an active ingredient which can be an antitussive or antihistamine but can also be a volatile oil such as menthol or eucalyptus. The confection normally contains a further flavouring agent such as lemon, honey or cherry but which can also be menthol or eucalyptus.

The art has also described methods of enhancing the effects of volatile oils in cough drops and the like. Thus U.S. Pat. No. 4,762,719, to Forester, published Aug. 9, 1988, describes a cough drop with a hard candy outer shell and a powdered centrefill. The centrefill composition comprises an active ingredient, such as menthol and eucalyptus, and a rapidly dissolving powder, such as sorbitol, xylitol or dextrose monohydrate, which desirably has a negative heat of solution to accentuate the cooling effect of the actives. The shell may further comprise a flavour such as cherry, lemon, orange, lime, etc.

U.S. Pat. No. 4,980,169, to Oppenheimer et al., assigned to the Warner-Lambert Company, published Dec. 25, 1990, describes cough drops in which the flavour is enhanced by incorporation a sensorially undetectable amount of a volatile oil modifying agent, especially capsicum.

It has now been found that the perceived effect of a physiological warming or cooling agent can be enhanced by incorporating a warming or cooling agent into a first composition which is administered along with a second composition which provides for delayed release of a cooling or warming agent. The first and second compositions are suitably provided by a centre-filling confectionery composition in which the shell provides the first composition and the filling provides the second.

It is accordingly an object of this invention to provide medicated confectionery compositions, especially throat drops, delivering enhanced throat and nasal warming or cooling.

SUMMARY OF THE INVENTION

The present invention relates to a throat drop, suitable for the relief of cough and cold like symptoms, comprising a cooling composition and a warming composition in distinct and discrete regions thereof, the cooling and warming compositions being adapted to provide sequential release profiles.

The throat drop provides an enhanced warming or cooling effect, analogous to the way in which an enhanced perception of heat or cold is experienced when one transfers one hand from hot to cold water or vice-versa.

All levels and ratios are by weight, unless otherwise indicated. Percentages are by weight of the throat drop unless otherwise specified.

DETAILED DESCRIPTION OF THE INVENTION

The present invention provides a throat drop comprising a cooling composition and a warming composition. The compositions are in distinct and discrete regions of the drop, preferably in the shell and filling respectively of a centre-filled drop, so that sequential release of the compositions is obtained when the drop is sucked. Examples of suitable product constructions providing differential release profiles are described in WO97/06695 incorporated herein by reference. Preferred for use herein, however, are centre-filled drops comprising a shell and a filling contained within the shell. The shell comprises a cooling or warming composition, and the filling comprises a warming composition if the shell comprises a cooling composition or a cooling composition if the shell comprises a warming composition.

Cooling compositions

An essential component of the cooling composition is a physiological cooling agent. Suitable levels of the cooling agent are from about 0.001 to about 10%, preferably from about 0.01 to about 5%, more preferably from about 0.05 to about 3% by weight of the cooling composition.

A test for physiological cooling agents is described in GB-A-1,452,291, published Oct. 13, 1976, reproduced herein below for convenience.

The following test procedure can be used as a means to identify compounds having a physiological cooling activity. This test is intended purely as a means for identifying compounds having a physiological cooling agent activity and useful in the present invention and for giving an indication of the different relative activities of the compounds, as between themselves and as compared with menthol, when applied in particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds of another area of the body, for example, the face or forearm, and this will be a useful guide in the choice of compounds to be used in preparations for external topical usage. It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties e.g. taste and smell of organic and inorganic compounds, see Kirk-Othmer: Encyclopedia of Chemical Technology, 2nd Ed. (1967) Vol. 14, pages 336–344.

The following test procedure is aimed at determining the minimum quantity of the test compound required to produce a noticeable cooling effect in a person of average sensitivity, this minimum quantity being termed the threshold for that particular compound. The tests are carried out on a selected panel of 6 people of median sensitivity to l-menthol.

To select a test panel of average sensitivity the following procedure is used. Known quantities of 1-menthol in solution in petroleum ether (bp. 40–60° C.) are placed on 5 mm squares of filter paper, whereafter the solvent is allowed to evaporate. A panel of observers is enrolled and asked to place one impregnated square at a time on the tongue and to report on the presence or absence of a cooling effect. The quantity of l-menthol on each impregnated square is gradually reduced from a value substantially above 0.25 $\mu$g. per square to substantially below 0.25 $\mu$g, the precise range being immaterial. Conveniently, one starts with squares containing 2.0 $\mu$g being half that of the preceding square, i.e. the second test square will contain 1.0 $\mu$g, the third 0.5 $\mu$g, and so on. Each quantity is tested on the tongue at least 10 times. In this way, the thresholds to cold receptor stimulus by l-menthol are determined for each individual of the panel, the threshold for each individual being that amount of 1-mentol for which, in a series of not less than 10 test applications, a cooling effect is reported 50% of the time. Six panel members are now selected whose threshold to l-menthol is in the range 0.1 $\mu$g to 10 $\mu$g and whose average threshold is approximately 0.25 $\mu$g, this select panel being regarded as the test panel of average sensitivity.

To test the activity of cooling agents, the above procedure is repeated using only the 6 selected panel members of average sensitivity to l-menthol. The individual thresholds for each test compound on each of the 6 selected panel members are determined and averaged. Those compounds whose average threshold on the select test panel is 100 $\mu$g or less, preferably 50 $\mu$g or less are regarded as having cooling activity in accordance with this invention.

Suitable physiological cooling agents are described in WO97/06695. Preferred for use herein are physiological cooling agents selected from the group consisting of menthol, peppermint oil, N-substituted-p-menthane-3-carboxamides, acyclic tertiary and secondary carboxamides, 3-1-menthoxy propan-1,2-diol and mixtures thereof. Particularly preferred for use herein are menthol and menthol containing oils such as peppermint oil.

The carboxamides found most useful are those described in U.S. Pat. No. 4,136,163, Jan. 23, 1979 to Watson et al., and U.S. Pat. No. 4,230, 688, Oct. 28, 1980 to Rowsell et al. The carboxamides in U.S. Pat. No. 4,136,163 are N-substituted-p-menthane-3-carboxamides. N-ethyl-p-menthane-3-carboxamide, commercially available as WS-3 from Wilkinson Sword, is preferred herein. The carboxamides of U.S. Pat. No. 4,230,688 are certain acyclic tertiary and secondary carboxamides, of which trimethyl isopropyl butanamide, commercially available as WS-23 from Wilkinson Sword is preferred for use herein.

The balance of the cooling composition is made up of a suitable appropriate carrier, such as water or a bulk sweetener, described in more detail below. The cooling composition can further comprise a warming agent as described herein provided that the predominant effect is one of cooling.

Warming Compositions

An essential component of the warming composition is a physiological warming agent. Suitable levels of the warming agent are from about 0.001 to about 10%, preferably from about 0.01 to about 5%, more preferably from about 0.05 to about 3% by weight of the warming composition.

Physiological warming agents can be tested for using a modification of the test for cooling agents described above, the test being modified to use benzyl alcohol rather than menthol as the reference sample tongue and asking the panellists to report on the presence or absence of a warming effect rather than a cooling effect. Preferred physiological warming agents are those selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, cinnamic aldehyde, phosphate derivatives thereof, and the commercially available warming agent David Michael Heat, available from David Michael & Co., Inc., 10801 Decatur Road, Philadelphia, Pa. 19154, USA. The phosphate derivatives mentioned are those described in WO 97/02273, incorporated by reference herein. The balance of the warming composition is made up of a suitable appropriate carrier, such as water or a bulk sweetener, described in more detail below. The warming composition can further comprise a cooling agent as described herein provided that the predominant effect is one of warming.

Sequential Release Profiles

An essential feature of the present invention is that the coolant and warming compositions are adapted to provide sequential release profiles. As used herein, 'adapted to provide sequential release profiles' means that the compositions are chemically and/or physically modified relative to a homogeneous mix of the compositions, in order that the person ingesting the confectionery product can perceive the maximum effect of the cooling agent at a different point in time to the peak sensation of warming. It will be understood that many such compositions will release the warming or cooling agent over the period of ingestion of the product and that there may be some simultaneous perception of warming agent and cooling agent. By positively separating the peak effects of cooling agent and warming agent, however, the overall organoleptic effect of the product is substantially improved versus compositions of the prior art which are not adapted to provide different release profiles. This can conveniently be achieved within a centre-filled confection.

Centre-filled Confectionery Products

The products of the present invention preferably take the form of a centre-filled throat drop comprising from 60 to 95%, preferably from 75 to 85%, of an edible shell and from 5 to 40%, preferably from 15 to 25%, of an edible filling, by weight of the drop.

The filling can be a solid, particularly a powder, or a liquid, including forms of intermediate consistency such as a paste or a gel. Preferably the filling is an aqueous filling comprising water at a level of from about 5 to about 95%, preferably from about 8 to about 20%, more preferably from about 10 to about 15% by weight of the filling. Levels of water higher than about 20% are unsuitable for the production of centre-filled hard candies.

When an aqueous centre-filling is used, the centre-filled throat drops of the present invention preferably also comprise from 0.001 to 10% by weight of the filling of a vesicle-forming agent which acts to form vesicles which are dispersed within the filling and encapsulate the warming or cooling agent. By 'vesicle' is meant an essentially spherical structure comprising a lipid bilayer encapsulating a central core. The vesicles herein can be uni- or multi-lamellar and have a number average particle size of from about 1 to about 100 μm, more preferably from about 5 to about 50 μm. The particle size can be measured using an optical microscope, such as a Nikon Optiphoto 2, linked to an electronic image analysis system such as the Linkam MS100. Measurement can also be made using a graduated graticule in the field of view. EP-A-534,823, which describes anhydrous make-up compositions which can form vesicles on exposure to water gives a comprehensive list of amphiphilic liquids which can be used to form vesicles. For the throat drops herein it is of course preferable that food-grade materials are used and the preferred vesicle forming agents are natural phospholipids such as egg or soy lecithin. The preferred phospholipids of the present invention are plant-derived lecithins and, especially, soybean lecithin. Soybean lecithin can act to form vesicles at very low levels.

Preferably the vesicle forming agent is present at a level of from about 0.001 to about 1%, more preferably from about 0.005 to about 0.1% and especially from about 0.01 to about 0.05% by weight of the filling. With adequate mixing, in the presence of water and a warming or cooling agent as described herein, the lecithin forms vesicles which encapsulate the warming or cooling agent.

It has further been found that the vesicle formation is enhanced by the presence of glycerine, which is preferably present at a level of from about 5 to about 25%, preferably from about 10 to about 20%, more preferably from about 12 to about 18% by weight of the filling.

The palatability of the filling is substantially improved if the composition further comprises a bulk sweetener, such as a sugar, suitably at a level of from about 5 to 80%, preferably from about 50 to about 75% on a dry solids basis by weight of the filling. A preferred source of the sweetener is high fructose corn syrup which, being commercially available as an 85% active material of which the balance is essentially water, can also provide some, or even all, of the water required by aqueous fillings, when employed.

Sugar free compositions comprising a sugar alcohol such as sorbitol can also be used. Preferably however, sugar alcohols are employed in admixture with glycerine, since it has been found that sugar alcohols on their own can suppress vesicle formation.

The fillings herein can also include a flavouring agent. As used herein, the term 'flavouring agent' means those flavour essences and equivalent synthetic ingredients which are added to the flavour composition for the principal purpose of providing flavour to the confectionery product. It excludes warming and cooling agents as described above. Flavouring agents well known in the confectionery art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derive flavours such as licorice. The amount of flavouring agent employed is normally a matter of preference subject to such factors as flavour type, base type and strength desired. In general, amounts up to about 4% by weight are usable with amounts of from about 0.1% to about 1% being preferred.

The edible shell can be a chewing gum or a hard or soft candy, preferably it is a hard candy. Centre-filled chewing gums are described, for example, in U.S. Pat. No. 3,894,154. Centre-filled hard candies are described in U.S. Pat. No. 4,372,942 and U.S. Pat. No. 4,466,983. A suitable sugar base for a hard candy shell comprises from about 30% to about 85% glucose syrup and from about 15% to about 70% sucrose. Alternatively, a sugar-free base can be used for the shell. Suitable sugar-free bases include bulk sweeteners such as isomalt, maltitol and sorbitol. Isomalt and maltitol are preferred. The inner surface of the shell can also have a separate edible lining to prevent or reduce interaction of the filling with the shell. The edible shell can also further comprise flavours as described above. In preferred throat drops according to the invention the edible shell is a cooling composition comprising a cooling agent and the centre-fill is a warming composition comprising a warming agent.

Aqueous fillings can be made by straightforward mixing techniques. The general techniques for manufacturing centre-filled confectionery products can be found in the "Silesia Confiserie Manual No. 3", published by Silesia-Essenzenfabrik Gerhard Hanke K. G., Abt. Fachbücherei.

Centre-filled throat drops according to the invention can be manufactured by deposit, rope-forming and extrusion processes as known in the art. Extrusion and rope-forming processes are preferred. An example of an extrusion process is described in U.S. Pat. No. 5,458,894. An example of an extrusion process is described in U.S. Pat. No. 5,002,791.

The following examples are given to illustrate the compositions and uses according to the invention. However, the invention is not limited thereto.

EXAMPLE 1

Liquid, centre-filled throat drops were prepared according to formulae A and B below. The liquid filling was made by adding a premix of the lecithin, colour solution, flavour oils, cooling and/or warming agents to a mixture of the high fructose corn syrup pre-warmed to 82° C. The components were mixed for two minutes and co-extruded with a separately made candy base comprising a cooling agent, to produce centre-filled throat drops.

|  | A Wt. % | B Wt. % |
| --- | --- | --- |
| Candy casing (80% by wt. of drop) | | |
| Sucrose | 58.12 | 49.37 |
| Glucose syrup (80% solids) | 41.51 | 49.37 |
| Peppermint oil | 0.17 | — |
| Menthol | 0.17 | 0.08 |
| Lemon oil | — | 0.27 |
| Citric acid | — | 0.91 |
|  | 100% | 100% |
| Liquid filling (20% by wt. of drop) | | |
| High fructose corn syrup[1] | 84.38 | 84.306 |
| Glycerine | 15.0 | 15.0 |
| Lecithin | 0.02 | 0.02 |
| Lemon oil | — | 0.314 |
| Colour (5% aqueous) | 0.32 | 0.16 |
| Peppermint oil | 0.15 | — |

-continued

|  | A Wt. % | B Wt. % |
|---|---|---|
| David Michael Heat[2] | 0.125 | 0.20 |
| Vanillin | 0.005 | — |
|  | 100% | 100% |

[1] 85% sugar solids, the balance being essentially water
[2] A warming agent available from David Michael & Co., Inc., Philadelphia, USA The throat drops of formulae A and B were sucked by individuals experiencing throat or nasal irritation. An enhanced throat warming effect, relative to drops without a cooling agent in the shell, and an enhanced feeling of nasal clearing were reported.

What is claimed is:

1. A throat drop for the relief of cough and cold symptoms comprising:
   a) a cooling composition having from about 0.001% to about 10% by weight, a physiological cooling agent selected from the group consisting of menthol, peppermint oil, N-substituted-p-menthane-3-carboxamides, acyclic tertiary and secondary carboxamides, 3-1-menthoxy propan-1,2-diol, and mixtures thereof, and
   b) a warming composition having from about 0.001% to about 10% by weight, a physiological warming agent selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, isopropyl alcohol, iso-amylalcohol, benzyl alcohol, chloroform, eugenol, phosphate derivatives thereof, the commercially available warming agent David Michael Heat, and mixtures thereof,
wherein said cooling composition and said warming composition are located in distinct and discrete regions within said throat drop and said cooling and warming compositions being adapted to provide sequential release profiles.

2. A throat drop according to claim 1, wherein the drop is a centre-filled confection comprising from 75 to 85% of an edible shell and from 15 to 25% of a filling by weight of the drop, the shell comprising a cooling composition and the filling comprising a warming composition.

3. A throat drop according to claim 1, wherein the drop is a centre-filled confection comprising from 75 to 85% of an edible shell and from 15 to 25% of a filling by weight of the drop, the shell comprising a warming composition and the filling comprising a cooling composition.

4. A throat drop according to claim 3, wherein the filling comprises from 8 to 20% water.

5. A throat drop according to claim 4, wherein the filling further comprises from 0.001 to 10% by weight of the filling of a vesicle-forming agent which acts to form vesicles which are dispersed within the filling and encapsulate the warming or cooling agent.

6. A throat drop according to claim 3, wherein the filling comprises from 5 to 25% glycerine.

7. A throat drop according to claim 3, wherein the filling comprises from 5 to 80% sugar.

8. A throat drop according to claim 7 wherein the sugar is provided by high fructose corn syrup.

9. A throat drop according to claim 3, wherein the shell comprises a sugar-free base.

10. A throat drop according to claim 9 wherein the filling comprises a sugar alcohol.

11. A throat drop according to claim 10 wherein the sugar alcohol is in admixture with glycerine.

12. A throat drop according to claim 2, wherein the filling is a solid.

13. A throat drop according to claim 2, wherein the filling is a powder.

14. A throat drop according to claim 2, wherein:
   (a) the shell comprises, by weight, from about 0.01% to about 5% cooling agent, from about 30% to about 85% glucose syrup and from about 15% to about 70% sucrose; and
   (b) the filling comprises, by weight on a dry solids basis, from about 0.001% to about 10% warming agent, from about 50% to about 75% high fructose corn syrup and from about 0.1% to about 1% flavouring agent.

15. A throat drop according to claim 2, wherein the filling comprises a warming agent and a sugar alcohol admixed with glycerine.

16. A throat drop according to claim 2, wherein the filling comprises, by weight, from about 0.001% to about 10% warming agent, from 8% to 20% water, and from 0.001% to 10% vesicle-forming agent; wherein the vesicle-forming agent forms vesicles which encapsulate the warming agent.

17. A throat drop according to claim 3, wherein the filling comprises, by weight, from about 0.001% to about 10% cooling agent, from 8% to 20% water, and from 0.001% to 10% of a vesicle-forming agent; wherein the vesicle-forming agent forms vesicles which encapsulate the cooling agent.

18. A throat drop according to claim 1, wherein the drop is a confection having a shell and a solid filling.

19. A confection in the form of a filled shell, the confection comprising:
   (a) a cooling composition comprising from about 0.001% to about 10%, by weight, cooling agent selected from the group consisting of menthol, peppermint oil, N-substituted-p-methane-3-carboxamides, acyclic tertiary and secondary carboxamides, 3-1-methoxy propan-1,2-diol, and mixtures thereof, and
   (b) a warming composition comprising from about 0.001% to about 10%, by weight, warming agent selected from the group consisting of vanillyl alcohol-n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, isopropl alcohol, iso-amylalcohol, benzyl alcohol, chloroform, eugenol, phosphate derivatives thereof, the commercially available warming agent David Michael Heat, and mixtures thereof;
wherein the cooling and warming compositions are adapted to provide sequential release profiles, and when the cooling composition is in the form of a shell, the warming composition is in the from of a filling, and when the cooling composition is in the form of a filling, the warming composition is in the from of a shell.

20. A confection according to claim 19, wherein:
   (a) the cooling composition comprises from about 0.05% to about 3%, by weight, cooling agent selected from the group consisting of menthol and peppermint oil; and (b) the warming composition comprises from about 0.05% to about 3%, by weight, warming agent and from 0.001% to 10%, by weight, phospholipid.

21. A confection according to claim 20, wherein the cooling composition in the form of a shell and the warming composition in the form of a liquid filling, and wherein the confection provides for an enhanced warming effect as compared to confections which do not contain a cooling agent in the shell.

22. A confection according to claim 19, wherein the shell has an edible lining on the inner surface of the shell.

23. A confection according to claim 19, wherein the filling is a solid.

24. A method of enhancing the warming effect of a throat drop, comprising the step of preparing a throat drop comprising:

(a) a cooling composition in the form of a hard candy shell comprising from about 0.001% to about 10%, by weight, cooling agent selected from the group consisting of methanol, peppermint oil, N-substituted-p-methane-3-carboxamides acyclic tertiary and secondary carboxamides, 3-1-methoxy propan-1,2-diol, and mixtures thereof, and (b) a warming composition in the form of a liquid filling comprising from about 0.001% to about 10%, by weight, warming agent selected from the group consisting of vanillyl alcohol n-butyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, isopropyl alcohol, isoamylalcohol, benzyl alcohol, chloroform, eugenol, phosphate derivatives thereof, the commercially available warming agent David Michael Heat, and mixtures thereof.

25. A method according to claim 24, wherein the cooling composition comprises from about 0.01% to about 5%, by weight, cooling agent, and the warming composition comprises from about 0.01% to about 5%, by weight, warming agent.

26. A method according to claim 24, wherein the warming composition further comprises, by weight of the warming composition, from about 8% to about 20% water, from about 0.001% to about 10% vesicle-forming agent, and from about 5% to about 25% glycerine; and wherein the vesicle-forming agent forms vesicles which encapsulate the warming agent.

27. A method according to claim 26, wherein the vesicle-forming agent comprises a phospholipid.

28. A method according to claim 24, wherein the cooling composition comprises, by weight, from about 0.01% to about 5% cooling agent; and the warming composition comprises, by weight, from about 0.01% to about 5% warming agent, about 10% to about 15% water, from about 0.005% to 0.1% phospholipid, and from about 10% to 20% glycerine.

* * * * *